United States Patent
Rickard et al.

(10) Patent No.: US 10,760,109 B2
(45) Date of Patent: Sep. 1, 2020

(54) COMPOSITIONS AND METHODS FOR CHARACTERIZING AND DIAGNOSING PERIODONTAL DISEASE

(71) Applicants: THE REGENTS OF THE UNIVERSITY OF MICHIGAN, Ann Arbor, MI (US); COLGATE-PALMOLIVE COMPANY, New York, NY (US)

(72) Inventors: Alexander Rickard, Ann Arbor, MI (US); William Giannobile, Ann Arbor, MI (US); Michelle Swetky, Ann Arbor, MI (US); Nielson T. Baxter, Ann Arbor, MI (US); Steven E. Miller, Skillman, NJ (US); Laurence Du-Thumm, Princeton, NJ (US); Hans Stettler, Hoboken, NJ (US)

(73) Assignees: THE REGENTS OF THE UNIVERSITY OF MICHIGAN, Ann Arbor, MI (US); COLGATE-PALMOLIVE COMPANY, New York, NY (US)

( * ) Notice: Subject to any disclaimer, the term of this patent is extended or adjusted under 35 U.S.C. 154(b) by 0 days.

(21) Appl. No.: 15/316,537

(22) PCT Filed: Jun. 8, 2015

(86) PCT No.: PCT/US2015/034643
§ 371 (c)(1),
(2) Date: Dec. 6, 2016

(87) PCT Pub. No.: WO2015/188178
PCT Pub. Date: Dec. 10, 2015

(65) Prior Publication Data
US 2017/0204447 A1    Jul. 20, 2017

Related U.S. Application Data

(60) Provisional application No. 62/008,994, filed on Jun. 6, 2014.

(51) Int. Cl.
*C12Q 1/04*    (2006.01)
*G16H 50/30*    (2018.01)
(Continued)

(52) U.S. Cl.
CPC ................ *C12Q 1/04* (2013.01); *C12Q 1/18* (2013.01); *C12Q 1/66* (2013.01);
(Continued)

(58) Field of Classification Search
CPC ... C12Q 1/68; C12Q 1/04; C12Q 1/18; C12Q 1/66; C07H 21/04; G06F 19/00
(Continued)

(56) References Cited

U.S. PATENT DOCUMENTS 8,293,478 B2 * 10/2012 Souno .................. A61K 31/341
                                                435/6.15
2007/0269813 A1 * 11/2007 Dewhirst ............... C12Q 1/689
                                                435/6.11
(Continued)

FOREIGN PATENT DOCUMENTS

JP    2009 114120       5/2009
WO    2007056680 A1    5/2007
(Continued)

OTHER PUBLICATIONS

Winkelhoff et al., (J. of Clin. Periodontology. Dec. 2002. vol. 29, Issue 11: pp. 1023-1028).*
(Continued)

*Primary Examiner* — Jana A Hines
(74) *Attorney, Agent, or Firm* — Casimir Jones, S.C.; Tanya Arenson

(57) ABSTRACT

The present disclosure relates to methods for characterizing and diagnosing dental diseases. In particular, the present disclosure relates to methods for characterizing and diagnosing dental disease (e.g., gingivitis and periodontal disease) based on levels of AI-2 in oral fluids and plaque.

13 Claims, 8 Drawing Sheets

(51) Int. Cl.
*C12Q 1/18* (2006.01)
*G01N 33/569* (2006.01)
*C12Q 1/66* (2006.01)
*G06F 19/00* (2018.01)

(52) U.S. Cl.
CPC ....... *G01N 33/56955* (2013.01); *G06F 19/00* (2013.01); *G16H 50/30* (2018.01); *G01N 2333/195* (2013.01); *G01N 2500/00* (2013.01); *G01N 2500/10* (2013.01); *G01N 2800/18* (2013.01); *Y02A 90/26* (2018.01)

(58) Field of Classification Search
USPC ................. 435/6.11, 6.15; 536/23.7, 24.32
See application file for complete search history.

(56) References Cited

U.S. PATENT DOCUMENTS

| | | | | |
|---|---|---|---|---|
| 2010/0137249 | A1* | 6/2010 | Wang | C07D 333/34 514/64 |
| 2012/0015397 | A1 | 1/2012 | Souno et al. | |
| 2012/0116799 | A1 | 5/2012 | Lindskog et al. | |
| 2017/0204447 | A1 | 7/2017 | Rickard et al. | |

FOREIGN PATENT DOCUMENTS

| | | |
|---|---|---|
| WO | 2009005178 A1 | 1/2009 |
| WO | 2009018342 A1 | 2/2009 |
| WO | 2012/134063 | 10/2012 |
| WO | 2015188178 A1 | 12/2015 |

OTHER PUBLICATIONS

Olsen (Microbial Ecology in Health and Disease . vol. 18, 2006—Issue 1 pp. 26-31). (Year: 2006).*
Lee et al., (FEMS Mocrobiol Rev 34(2010) 426-444 (Year: 2010).*
EP Search Report, EP Patent Application No. 15802368.9, dated Nov. 27, 2017.
Jang, Yun-Ji et al. "Autoinducer 2 of Fusobacterium nucleatum as a target molecule to inhibit biofilm formation of periodontopathogens" Archives of Oral Biology, vol. 58, No. 1, 2013, pp. 17-27.
Cuadra-Saenz et al., "Autoinducer-2 influences interactions amongst pioneer colonizing Streptococci in oral biofilms." Microbiology. Jul. 2012;158(Pt 7):1783-95.
Darby et al., "Non-surgical management of periodontal disease." Aust Dent J. Sep. 2009;54 Suppl 1:S86-95.
Eke et al., "Prevalence of periodontitis in adults in the United States: 2009 and 2010." J Dent Res. Oct. 2012;91(10):914-20.
Frias et al., "Periodontal pathogens produce quorum sensing signal molecules." Infect Immun. May 2001;69(5):3431-4.
Jakubovics et al., "The road to ruin: the formation of disease-associated oral biofilms." Oral Dis. Nov. 2010;16(8):729-39.
Kolenbrander et al., "Bacterial interactions and successions during plaque development." Periodontol 2000. 2006;42:47-79.
Kuo et al., "Associations between periodontal diseases and systemic diseases: a review of the inter-relationships and interactions with diabetes, respiratory diseases, cardiovascular diseases and osteoporosis." Public Health. Apr. 2008;122(4):417-33.
Petrova et al., "Sticky situations: key components that control bacterial surface attachment." J Bacteriol. May 2012;194(10):2413-25.
Rickard et al., "Autoinducer-2 is produced in saliva-fed flow conditions relevant to natural oral biofilms." J Appl Microbiol. Dec. 2008;105(6):2096-103.
Rickard et al., "Production of cell-cell signalling molecules by bacteria isolated from human chronic wounds." J Appl Microbiol. May 2010;108(5):1509-22.
Rickard et al., "Autoinducer 2: a concentration-dependent signal for mutualistic bacterial biofilm growth." Mol Microbiol. Jun. 2006;60(6):1446-56.
Stoodley et al., "Biofilms as complex differentiated communities." Annu Rev Microbiol. 2002;56:187-209.
Winkelhoff et al., "Porphyromonas gingivalis, Bacteroides forsythus and other putative periodontal pathogens in subjects with and without periodontal destruction." J Clin Periodontol. Nov. 2002;29(11):1023-8. Abstract .
International Search Report of related PCT/US2015/034643 , dated Aug. 25, 2015, 17 pages.

* cited by examiner

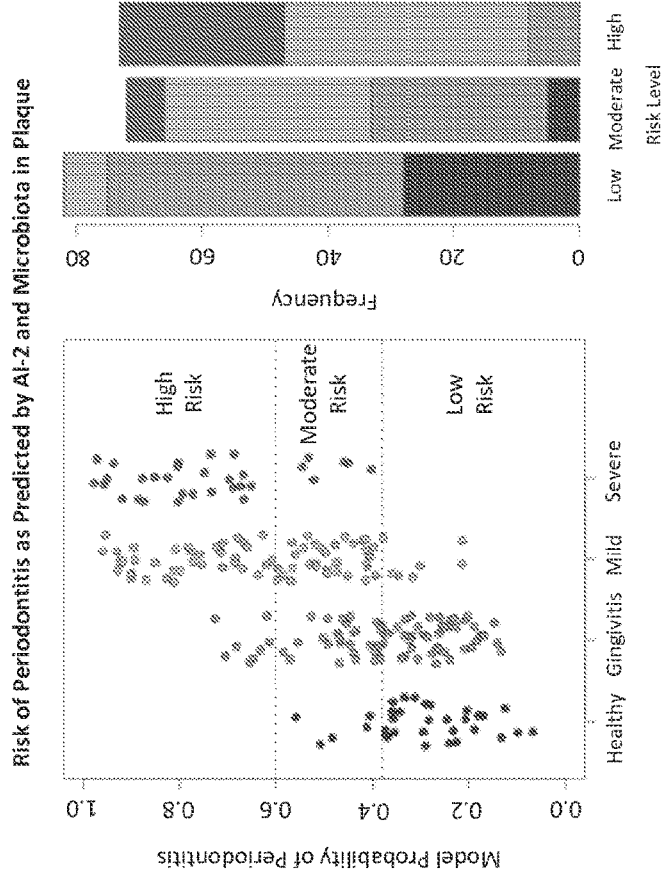
FIG. 10 (con't)

COMPOSITIONS AND METHODS FOR CHARACTERIZING AND DIAGNOSING PERIODONTAL DISEASE

The present application is a 371 U.S. National Phase Entry of pending International Application No. PCT/US2015/034643, filed Jun. 8, 2015, which claims priority to U.S. Provisional Application Ser. No. 62/008,994, filed Jun. 6, 2014, each of which are herein incorporated by reference in their entireties.

FIELD OF INVENTION

The present disclosure relates to methods for characterizing and diagnosing dental diseases. In particular, the present disclosure relates to methods for characterizing and diagnosing dental disease (e.g., gingivitis and periodontal disease) based on levels of AI-2 in oral fluids and plaque.

BACKGROUND OF THE INVENTION

Dental plaque or plaque bio-film is a soft deposit that forms on surfaces of the oral cavity, such as tissue and teeth, and comprises a complex mixture of an accumulation of bacteria and salivary as well as food by-products, starch, proteins and proteinacious material. Thus, inhibiting the growth of bio-film not only involves dispersing the accumulation of existing proteinacious materials, but also requires prohibiting and minimizing their reattachment to the tooth surface. Plaque adheres tenaciously at the points of irregularity or discontinuity (e.g., on rough calculus surfaces, at the gum line, on tongue surface and within crevices, and the like). Besides being unsightly, plaque is implicated in the occurrence of gingivitis and other forms of periodontal disease.

Gingivitis is the earliest stage of gum disease, an inflammation of the gums caused by plaque buildup at the gumline. If daily brushing and flossing do not remove the plaque, it produces toxins (poisons) that can irritate the gum tissue, causing gingivitis. Symptoms include bleeding during brushing and flossing. At this early stage in gum disease, damage can be reversed, since the bone and connective tissue that hold the teeth in place are not yet affected.

Periodontitis is more advanced gum disease. At this stage, the supporting bone and fibers that hold teeth in place are irreversibly damaged. Gums may begin to form a pocket below the gumline, which traps food and plaque. Proper dental treatment and improved home care can usually help prevent further damage.

In advanced Periodontitis, the fibers and bone supporting your teeth are destroyed, which can cause teeth to shift or loosen. This can affect bite and, if aggressive treatment can't save them, teeth may need to be removed.

A wide variety of agents have been suggested to retard plaque formation and the oral infections and dental disease associated with plaque formation. Current treatments for removing and preventing plaque build-up include brushing the teeth with an abrasive and/or antibacterial toothpaste, flossing, and various other treatments. The effectiveness of such treatments depends on a variety of factors including the amount of plaque present. While current techniques for removing and preventing plaque buildup on the teeth and oral tissues are suitable for their intended uses, they are subject to improvement.

Additional methods for identifying and treating early stage dental disease are needed.

SUMMARY OF THE INVENTION

The present disclosure relates to methods for characterizing and diagnosing dental diseases. In particular, the present disclosure relates to methods for characterizing and diagnosing dental disease (e.g., gingivitis and periodontal disease) based on levels of AI-2 in oral fluids and plaque.

For example, embodiments of the present invention provide uses and methods of characterizing, prognosing, and diagnosing periodontal disease, comprising; a) detecting an altered level of AI-2 in an oral sample; and b) diagnosing the presence of periodontal disease when the level of AI-2 is altered (e.g. increased or decreased) relative to the level in subjects not diagnosed with periodontal disease. In some embodiments, the oral sample is an oral fluid (e.g., saliva or gingival crevicular fluid (GCF)) or a plaque sample. In some embodiments, the method further comprises the step of detecting the presence of one or more (e.g., 1, 5, 10, 15, 20, or all of the listed) species of bacteria (e.g., *Akkermansia muciniphila, Bacteroides ovatus, Veillonella dispar, Coprobacter fastidiosus, Ruminococcus gnavus, Blautia schinkii, Streptococcus oralis, Bacteroides vulgatus, Rothia dentocariosa, Leptotrichia wadei, Bacteroides uniformis, Neisseria subflava, Actinomyces oris, Bacteroides stercoris, Haemophilus parainfluenzae, Selenomonas flueggei/noxia, Abiotrophia defective, Corynebacterium matruchotii,* Flavobacteriaceae, *Neisseria cinerea, Selenomonas* sp., *Oribacterium sinus, Leptotrichia buccalis, Porphyromonas catoniae, Streptococcus salivarius, Kingella denitrificans, Bergeyella* sp. AF14, *Fusobacterium nucleatum,* Porphyromonadaceae, *Prevotella melaninogenica,* or Bacteroidetes). In some embodiments, the oral sample is plaque and the bacteria are one or more species selected from, for example, *Akkermansia muciniphila, Bacteroides ovatus, Veillonella dispar, Coprobacter fastidiosus, Ruminococcus gnavus, Blautia schinkii, Streptococcus oralis, Bacteroides vulgatus, Rothia dentocariosa, Leptotrichia wadei, Bacteroides uniformis, Neisseria subflava, Actinomyces oris, Bacteroides stercoris, Haemophilus parainfluenzae, Selenomonas flueggei/noxia, Abiotrophia defective, Corynebacterium matruchotii,* or Flavobacteriaceae. In some embodiments, the oral sample is saliva and the bacteria are one or more species selected, for example, *Neisseria cinerea, Selenomonas* sp., *Veillonella dispar, Oribacterium sinus, Leptotrichia buccalis, Bacteroides ovatus, Porphyromonas catoniae, Streptococcus salivarius, Bacteroides vulgatus, Akkermansia muciniphila, Kingella denitrificans, Bergeyella* sp. AF14, *Haemophilus parainfluenzae, Fusobacterium nucleatum,* Porphyromonadaceae, *Ruminococcus gnavus, Prevotella melaninogenica,* Bacteroidetes, or *Rothia dentocariosa.*

In some embodiments, the method further comprises the step of administering a treatment for periodontal disease when the altered level of AI-2 is detected. The present invention is not limited to a particular treatment for periodontal disease. Examples include, but are not limited to, an antibiotic (e.g., doxycycline), a dental cleaning, or a laser treatment. In some embodiments, the treatment is in a mouthwash or toothpaste. In some embodiments, the sample is from a human or non-human animal.

Further embodiments provide a method of treating periodontal disease, comprising: a) detecting an altered level of AI-2 in an oral sample; b) diagnosing the presence of periodontal disease when the level of AI-2 is altered (e.g. increased or decreased) relative to the level in subjects not diagnosed with periodontal disease; and c) administering a treatment for periodontal disease when the altered level of AI-2 is detected.

In yet other embodiments, the present invention provides a method of screening compounds, comprising: a) contacting an oral sample comprising oral bacteria with a test compound; and b) measuring the level of AI-2 and/or the presence of one or more species of bacteria in the sample. In some embodiments, the dental sample is a biofilm. In some embodiments, compounds that alter the levels of AI-2 in said sample relative to the levels in the absence of the compounds are identified as therapeutic agents. In some embodiments, the method further comprises the step of repeating said detecting step one or more times.

Additional embodiments provide a kit, comprising: a) a first reagent for detecting the levels of AI-2 in a first oral sample; and optionally b) a second reagent for detecting levels of AI-2 in a second oral sample. In some embodiments, the reagent is a bioluminescent reporter that recognizes AI-2. In some embodiments, the kit comprises reagents for detecting the presence of bacteria (e.g., those described herein) in the sample.

In some embodiments, the present invention provides a system, comprising: a) a computer processor; and b) software configured to analysis levels of AI-2 in at least 2 oral samples and/or presence of one or more bacteria by comparing the levels to threshold levels specific for each of the oral samples. In some embodiments, the threshold levels are, for example, population averages for subjects not diagnosed with periodontal disease; or levels of an individual subject not diagnosed with periodontal disease, diagnosed with periodontal disease, or diagnosed with periodontal disease and not treated for the periodontal disease. In some embodiments, the system comprises reagents for analyzing the microbial population (e.g., detecting the presence or identify of bacteria in a dental sample). In some embodiments, the software further provides a diagnosis or prognosis or risk of periodontal disease. In some embodiments, the software further provides a recommended treatment course of action.

Additional embodiments are disclosed herein.

DEFINITIONS

Figure 1:
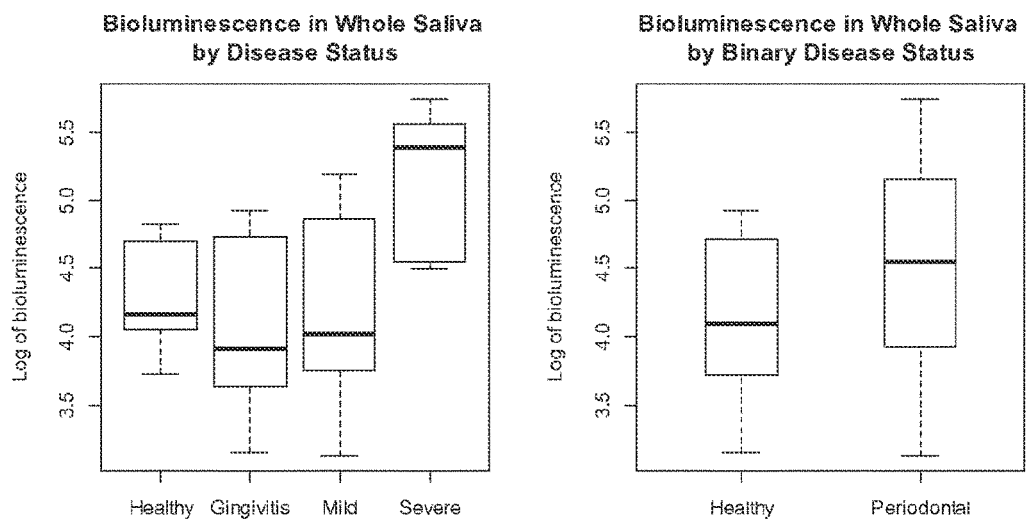
FIG. 1 shows AI-2 expression in whole saliva by disease status and binary disease status.

To facilitate an understanding of the present invention, a number of terms and phrases are defined below:

As used herein the term "biofilm" refers to any three-dimensional, (e.g., matrix-encased) microbial community displaying multicellular characteristics. Accordingly, as used herein, the term biofilm includes surface-associated biofilms as well as biofilms in suspension, such as flocs and granules. Biofilms may comprise a single microbial species or may be mixed species complexes, and may include bacteria as well as fungi, algae, protozoa, or other microorganisms.

As used herein, the term "oral fluid" refers to any fluid that originated in the oral cavity. Examples include, but are not limited to, saliva and gingival crevicular fluid (GCF).

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

As used herein, the term "prokaryotes" refers to a group of organisms that usually lack a cell nucleus or any other membrane-bound organelles. In some embodiments, prokaryotes are bacteria. The term "prokaryote" includes both archaea and eubacteria.

As used herein, the term "subject" refers to individuals (e.g., human, animal, or other organism) to be treated by the methods or compositions of the present invention. Subjects include, but are not limited to, mammals (e.g., murines, simians, equines, bovines, porcines, canines, felines, and the like), and most preferably includes humans. In the context of the invention, the term "subject" generally refers to an individual who will receive or who has received treatment for a condition characterized by the presence of biofilm-forming bacteria, or in anticipation of possible exposure to biofilm-forming bacteria.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "virulence" refers to the degree of pathogenicity of a microorganism (e.g., bacteria or fungus), e.g., as indicated by the severity of the disease produced or its ability to invade the tissues of a subject. It is generally measured experimentally by the median lethal dose ($LD_{50}$) or median infective dose ($ID_{50}$). The term may also be used to refer to the competence of any infectious agent to produce pathologic effects.

As used herein, the term "toxic" refers to any detrimental or harmful effects on a subject, a cell, or a tissue as compared to the same cell or tissue prior to the administration of the toxicant.

As used herein, the term "pathogen" refers to a biological agent that causes a disease state (e.g., infection, cancer, etc.) in a host. "Pathogens" include, but are not limited to, viruses, bacteria, archaea, fungi, protozoans, mycoplasma, prions, and parasitic organisms.

As used herein, the term "microbe" refers to a microorganism and is intended to encompass both an individual organism, or a preparation comprising any number of the organisms.

As used herein, the term "microorganism" refers to any species or type of microorganism, including but not limited to, bacteria, archaea, fungi, protozoans, mycoplasma, and parasitic organisms.

As used herein, the term "fungi" is used in reference to eukaryotic organisms such as the molds and yeasts, including dimorphic fungi.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces,* and *Rickettsia*. All forms of bacteria are included within this definition including cocci, bacilli, spirochetes, spheroplasts, protoplasts, etc. Also included within this term are prokaryotic organisms that are Gram-negative or Gram-positive. "Gram-negative" and "Gram-positive" refer to staining patterns with the Gram-staining process, which is well known in the art. (See e.g., Finegold and Martin, Diagnostic Microbiology, 6th Ed., CV Mosby St. Louis, pp. 13-15 (1982)). "Gram-positive bacteria" are bacteria that retain the primary dye used in the Gram-stain, causing the stained cells to generally appear dark blue to purple under the microscope. "Gram-negative bacteria" do not retain the primary dye used in the Gram-stain, but are stained by the counterstain. Thus, Gram-negative bacteria generally appear red.

The term "non-pathogenic bacteria" or "non-pathogenic bacterium" includes all known and unknown non-pathogenic bacterium (Gram-positive or Gram-negative) and any pathogenic bacterium that has been mutated or converted to a non-pathogenic bacterium. Furthermore, a skilled artisan recognizes that some bacteria may be pathogenic to specific species and non-pathogenic to other species; thus, these bacteria can be utilized in the species in which it is non-pathogenic or mutated so that it is non-pathogenic.

As used herein, "subject" refers to any animal (e.g., human or non-human animal) that is the subject of diagnostic, research, screening, or therapeutic compositions and methods described herein.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

As used herein, the term "cell culture" refers to any in vitro culture of cells, including, e.g., prokaryotic cells and eukaryotic cells. Included within this term are continuous cell lines (e.g., with an immortal phenotype), primary cell cultures, transformed cell lines, finite cell lines (e.g., non-transformed cells), bacterial cultures in or on solid or liquid media, and any other cell population maintained in vitro.

The term "coating" as used herein refers to a layer of material covering, e.g., a medical device or a portion thereof. A coating can be applied to the surface or impregnated within the material of the implant.

As used herein, the term "antimicrobial agent" refers to composition that decreases, prevents or inhibits the growth of bacterial and/or fungal organisms. Examples of antimicrobial agents include, e.g., antibiotics and antiseptics.

The term "antiseptic" as used herein is defined as an antimicrobial substance that inhibits the action of microorganisms, including but not limited to α-terpineol, methylisothiazolone, cetylpyridinium chloride, chloroxyleneol, hexachlorophene, chlorhexidine and other cationic biguanides, methylene chloride, iodine and iodophores, triclosan, taurinamides, nitrofurantoin, methenamine, aldehydes, azylic acid, silver, benzyl peroxide, alcohols, and carboxylic acids and salts. One skilled in the art is cognizant that these antiseptics can be used in combinations of two or more to obtain a synergistic or additive effect. Some examples of combinations of antiseptics include a mixture of chlorhexidine, chlorhexidine and chloroxylenol, chlorhexidine and methylisothiazolone, chlorhexidine and (α-terpineol, methylisothiazolone and α-terpineol; thymol and chloroxylenol; chlorhexidine and cetylpyridinium chloride; or chlorhexidine, methylisothiazolone and thymol. These combinations provide a broad spectrum of activity against a wide variety of organisms.

The term "antibiotics" as used herein is defined as a substance that inhibits the growth of microorganisms, preferably without damage to the host. For example, the antibiotic may inhibit cell wall synthesis, protein synthesis, nucleic acid synthesis, or alter cell membrane function.

Classes of antibiotics include, but are not limited to, macrolides (e.g., erythromycin), penicillins (e.g., nafcillin), cephalosporins (e.g., cefazolin), carbepenems (e.g., imipenem), monobactam (e.g., aztreonam), other beta-lactam antibiotics, beta-lactam inhibitors (e.g., sulbactam), oxalines (e.g. linezolid), aminoglycosides (e.g., gentamicin), chloramphenicol, sufonamides (e.g., sulfamethoxazole), glycopeptides (e.g., vancomycin), quinolones (e.g., ciprofloxacin), tetracyclines (e.g., doxycycline, minocycline), fusidic acid, trimethoprim, metronidazole, clindamycin, mupirocin, rifamycins (e.g., rifampin), streptogramins (e.g., quinupristin and dalfopristin) lipoprotein (e.g., daptomycin), polyenes (e.g., amphotericin B), azoles (e.g., fluconazole), and echinocandins (e.g., caspofungin acetate).

Examples of specific antibiotics include, but are not limited to, erythromycin, nafcillin, cefazolin, imipenem, aztreonam, gentamicin, sulfamethoxazole, vancomycin, ciprofloxacin, trimethoprim, rifampin, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, gatifloxacin, moxifloxacin, gemifloxacin, enoxacin, fleroxacin, doxycycline, minocycline, linezolid, temafloxacin, tosufloxacin, clinafloxacin, sulbactam, clavulanic acid, amphotericin B, fluconazole, itraconazole, ketoconazole, and nystatin. Other examples of antibiotics, such as those listed in Sakamoto et al, U.S. Pat. No. 4,642,104 herein incorporated by reference will readily suggest themselves to those of ordinary skill in the art.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include oral fluids, plaque, blood products, such as plasma, serum and the like. Such examples are not however to be construed as limiting the sample types applicable to the present invention.

DETAILED DESCRIPTION OF THE INVENTION

The present disclosure relates to methods for characterizing and diagnosing dental diseases. In particular, the present disclosure relates to methods for characterizing and diagnosing dental disease (e.g., gingivitis and periodontal disease) based on levels of AI-2 in oral fluids and plaque.

In some embodiments, the levels of AI-2 are measured in oral samples that comprise biofilms. A biofilm is an aggregate of microorganisms in which cells adhere to each other and/or to a surface. These adherent cells are frequently embedded within a self-produced matrix of extracellular polymeric substance (EPS). Biofilm EPS, also referred to as slime, is a polymeric conglomeration generally composed of extracellular DNA, proteins, and polysaccharides in various configurations and of various compositions. Biofilms may form on living or non-living surfaces, and represent a prevalent mode of microbial life in natural, industrial and clinical settings. The microbial cells growing in a biofilm are physiologically distinct from planktonic cells of the same organism, which, by contrast, are single cells that may float or swim in a liquid medium.

Microbial biofilms form in response to many factors including but not limited to cellular recognition of specific or non-specific attachment sites on a surface, nutritional cues, or in some cases, by exposure of planktonic cells to sub-inhibitory concentrations of antibiotics. When a cell switches to the biofilm mode of growth, it undergoes a phenotypic shift in behavior in which large suites of genes are differentially regulated (Petrova et al., J. Bacteriol. 2012 May; 194(10):2413-25; Stoodley et al., Annu Rev Microbiol. 2002; 56:187-209).

Dental plaque is composed of hundreds of species of bacteria that can collectively cause oral and systemic diseases (Jakubovics et al., Oral diseases. 2010; 16(8):729-39; Kuo et al., Public Health. 2008; 122(4):417-33.). During dental plaque development, bacteria sense and respond to numerous exogenous bacterial- or environmental-derived chemicals which alter their ability to establish themselves within these biofilms.

Oral biofilms cause major problems throughout both industrialized and developing countries. Data from recent surveys indicate that 23.7% of US adults have untreated dental caries while 38.5% of adults have moderate to severe periodontitis (National Center for Health Statistics. Health, United States, 2011: With Special Feature on Socioeconomic Status and Health. Hyattsville, Md.: 2012; Eke et al., Journal of dental research. 2012; 91(10):914-20). Untreated dental caries also affects between 15-20% of children up to 19 years, while periodontitis is a major problem in the elderly population, where 64% of adults over 65 years have moderate to severe forms of the condition (National Center for Health Statistics. Health, United States, 2011: With Special Feature on Socioeconomic Status and Health. Hyattsville, Md.: 2012; Eke et al., Journal of dental research. 2012; 91(10):914-20). Clearly, new methods for controlling dental plaque-related diseases are urgently needed.

Autoinducer-2 (AI-2) is a family of bacterial signal molecules that has been indicated to mediate quorum sensing. Quorum sensing is the bacterial-mediated signal molecule induced alteration of the collective behavior of bacterial communities. Such interactions occur in biofilms such as dental plaque. Signal molecules can be differentially produced by bacteria from biofilm communities in oral bacteria (Frias et al. 2001) and wounds (Rickard et al. 2010).

Experiments conducted during the course of development of embodiments of the present invention demonstrated that there are differences in AI-2 concentration from dental plaque biofilm communities in healthy and diseased situations and from a variety of sources: saliva, dental plaque scrapings, and gingival crevicular fluid (GCF). As such, measuring AI-2 concentration finds use as a predictor of periodontal disease and to study the efficacy of anti-dental plaque biofilm treatments. The amount of AI-2 is directly related or inversely related to the disease status of patients, depending upon the source (e.g., saliva, dental plaque scraping, GCF). Further experiments demonstrated enhanced sensitivity of detection of periodontal disease when the presence of one or more species of bacteria is detected in combination with AI-2 levels. In some embodiments, computer analysis software is utilized to determine a risk, diagnosis or prognosis of periodontal disease using AI-1 levels and/or bacterial species analysis (See e.g., below sections).

For example, in some embodiments, the present invention provides systems and methods for diagnosing, characterizing, or screening for periodontal disease.

In some embodiments, levels of AI-2 in oral fluids or plaque are assayed (e.g., using any suitable method such as those disclosed herein). In some embodiments, the results are used to provide a diagnosis or prognosis of periodontal disease or gingivitis.

I. Detection of AI-2 Levels

Any suitable method of measuring the levels of AI-2 in oral samples is contemplated for use in the systems and methods described herein. In some embodiments, samples are processed before analysis (e.g., to isolate AI-2 molecules). A variety of techniques may be used for this purpose, including but not limited: centrifugation; immunocapture; cell lysis; and, nucleic acid target capture (See, e.g., EP Pat. No. 1 409 727, herein incorporated by reference in its entirety).

In some embodiments, AI-2 levels are detected using a bioluminescence detection method (e.g., those described in the experimental section)

II. Analysis of Microbial Community

In some embodiments, the presence of one or more bacteria in the oral sample is utilized in combination with AI-2 levels to diagnose, characterize, or screen for periodontal disease, screen compounds, etc. In some embodiments, bacteria identified in Example 3 as associated with periodontal disease are detected. In some embodiments, one or more (e.g., 1, 5, 10, 15, 20, or all of the listed) species of bacteria (e.g., *Akkermansia muciniphila, Bacteroides ovatus, Veillonella dispar, Coprobacter fastidiosus, Ruminococcus gnavus, Blautia schinkii, Streptococcus oralis, Bacteroides vulgatus, Rothia dentocariosa, Leptotrichia wadei, Bacteroides uniformis, Neisseria subflava, Actinomyces oris, Bacteroides stercoris, Haemophilus parainfluenzae, Selenomonas flueggei/noxia, Abiotrophia defective, Corynebacterium matruchotii*, Flavobacteriaceae, *Neisseria cinerea, Selenomonas* sp., *Oribacterium sinus, Leptotrichia buccalis, Porphyromonas catoniae, Streptococcus salivarius, Kingella denitrificans, Bergeyella* sp. AF14, *Fusobacterium nucleatum*, Porphyromonadaceae, *Prevotella melaninogenica*, or *Bacteroidetes*). In some embodiments, the oral sample is plaque and the bacteria are one or more species selected from, for example, *Akkermansia muciniphila, Bacteroides ovatus, Veillonella dispar, Coprobacter fastidiosus, Ruminococcus gnavus, Blautia schinkii, Streptococcus oralis, Bacteroides vulgatus, Rothia dentocariosa, Leptotrichia wadei, Bacteroides uniformis, Neisseria subflava, Actinomyces oris, Bacteroides stercoris, Haemophilus parainfluenzae, Selenomonas* flueggei/noxia, *Abiotrophia defective, Corynebacterium matruchotii*, or Flavobacteriaceae are detected. In some embodiments, the oral sample is saliva and the bacteria are one or more species selected, for example, *Neisseria cinerea, Selenomonas* sp., *Veillonella dispar, Oribacterium sinus, Leptotrichia buccalis, Bacte-*

*roides ovatus, Porphyromonas catoniae, Streptococcus salivarius, Bacteroides vulgatus, Akkermansia muciniphila, Kingella denitrificans, Bergeyella* sp. AF14, *Haemophilus parainfluenzae, Fusobacterium nucleatum,* Porphyromonadaceae, *Ruminococcus gnavus, Prevotella melaninogenica,* Bacteroidetes, or *Rothia dentocariosa.*

Bacteria are detected using any suitable method (e.g., one or more of those described below).

In some embodiments, nucleic acid sequencing methods are utilized for assaying microbial communities. In some embodiments, the sequencing is a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc. Morozova and Marra provide a review of some such technologies in *Genomics,* 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., *Clinical Chem.,* 55: 641-658, 2009; MacLean et al., *Nature Rev. Microbiol.,* 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), Life Technologies/Ion Torrent, the Solexa platform commercialized by Illumina, GnuBio, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing (Voelkerding et al., *Clinical Chem.,* 55: 641-658, 2009; MacLean et al., *Nature Rev. Microbiol.,* 7: 287-296; U.S. Pat. Nos. 6,210,891; 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., *Clinical Chem.,* 55: 641-658, 2009; MacLean et al., *Nature Rev. Microbiol.,* 7: 287-296; U.S. Pat. No. 6,833,246; U.S. Pat. No. 7,115,400; U.S. Pat. No. 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 250 nucleotides, with overall output exceeding 1 billion nucleotide pairs per analytical run.

Sequencing nucleic acid molecules using SOLiD technology (Voelkerding et al., *Clinical Chem.,* 55: 641-658, 2009; MacLean et al., *Nature Rev. Microbiol.,* 7: 287-296; U.S. Pat. Nos. 5,912,148; 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing (see, e.g., Astier et al., J. Am. Chem. Soc. 2006 Feb. 8; 128(5):1705-10, herein incorporated by reference) is utilized. The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, HeliScope by Helicos BioSciences (Voelkerding et al., *Clinical Chem.*, 55: 641-658, 2009; MacLean et al., *Nature Rev. Microbiol.*, 7: 287-296; U.S. Pat. Nos. 7,169,560; 7,282,337; 7,482,120; 7,501,245; 6,818,395; 6,911,345; 7,501,245; each herein incorporated by reference in their entirety) is utilized. Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., *Science* 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb to 100 Gb generated per run. The read-length is 100-300 base pairs. The accuracy for homopolymer repeats of 5 repeats in length is ~98%. The benefits of ion semiconductor sequencing are rapid sequencing speed and low upfront and operating costs.

Stratos Genomics, Inc. sequencing involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., *Clinical Chem.*, 55: 641-58, 2009; U.S. Pat. No. 7,329,492; U.S. patent application Ser. No. 11/671,956; U.S. patent application Ser. No. 11/781, 166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

In some embodiments, detection methods utilize hybridization assays. Illustrative non-limiting examples of nucleic acid hybridization techniques include, but are not limited to, microarrays including, but not limited to: DNA microarrays (e.g., cDNA microarrays and oligonucleotide microarrays). A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes or transcripts by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

In some embodiments, detection methods utilize amplification methods. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399,491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPaS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

Non-amplified or amplified nucleic acids can be detected by any means. For example, the nucleic acids can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety).

II. Diagnostic and Screening Applications

In some embodiments, the present disclosure provides systems and methods for diagnosing, prognosing, screening, and researching periodontal disease based on levels of AI-2 in oral samples.

In some embodiments, the level of AI-2 in a single oral sample type is assayed (e.g., saliva, GCF, or plaque). In some embodiments, the level of AI-2 in a combination of two or more different sample types is assayed (e.g., GCF and saliva, GCF and plaque, saliva and plaque, or saliva, GCF, and plaque). In some embodiments, the levels of AI-2 in the two or more different sample types is utilized to provide diagnostic or prognostic information.

A. Data Analysis

In some embodiments, a computer-based analysis program is used to translate the raw data generated by the detection assay (e.g., the level of AI-2 in an oral sample) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., oral sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a tooth scraping or saliva) and directly send it to a profiling center. Once received by the profiling service, the sample is processed and a profile is produced (e.g., level of AI-2), specific for the diagnostic or prognostic information desired for the subject.

The profile data is then prepared in a format suitable for interpretation by a treating clinician. For example, rather than providing raw data, the prepared format may represent a diagnosis or risk assessment (e.g., presence or severity of periodontal disease) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action. In some embodiments, the report includes a recommended treatment course of action.

In some embodiments, a threshold level below or above which indicates the presence of periodontal disease is utilized in diagnostic, prognostic, and monitoring embodiments. In some embodiments, the threshold is a population average of subjects without periodontal disease or gingivitis. In some embodiments, the threshold level is determined for an individual patient (e.g., before treatment or before the patient has developed periodontal disease) and the levels are compared to the individual threshold over time.

In some embodiments, the levels of AI-2 in multiple sample types are compared to threshold levels and then combined to generate a "risk score" or "risk profile."

B. Monitoring and Determining a Treatment Course of Action

In some embodiments, levels of AI-2 are utilized to monitor treatment over time. For example, in some embodiments, the levels of AI-2 are determined prior to treatment. Is some embodiments, levels of AI-2 are assayed one or more times after a period of time (e.g. once every day, week, month, year, or less often). In some embodiments, the results are used to determine a treatment course of action (e.g., start, stop, or alter treatment) depending on the results of the assay.

For example, in some embodiments, subjects with an altered level of AI-2 in oral fluids are administered a treatment for periodontal disease. Subjects lacking altered levels of AI-2 but having other symptoms of periodontal disease can be prescribed additional screening visits or dental cleanings to monitor for potential periodontal disease.

In some embodiments, subjects found to have periodontal disease are administered a treatment. In some embodiments, assays for AI-2 levels are repeated after a period of treatment (e.g., days, weeks, months, or years). In some embodiments, the results are used to modify or start or stop treatment. In some embodiments, assays for AI-2 are repeated periodically (e.g., daily, weekly, monthly, annually, etc.) in order to monitor the progression or treatment of periodontal disease.

The present disclosure is not limited to a particular treatment for gingivitis or periodontal disease. Examples include, but are not limited to, cleanings by a dental hygienist, oral antibiotics (e.g., doxycline), and laser treatments.

C. Screening Assays and Therapeutic Agents

Embodiments of the present disclosure provide compositions and method for identifying therapeutic agents (e.g., agents useful in the treatment of periodontal disease). For example, in some embodiments, levels of AI-2 are assayed in the presence and absence of test compounds. Test compounds that alter (e.g., increase or decrease) AI-2 levels are identified as potential therapeutic agents.

In some embodiments, test compounds are formulated as oral care products (e.g., mouthwash, toothpaste, etc.).

D. Compositions and Kits

Compositions for use in the diagnostic methods described herein include, but are not limited to, detection reagents (e.g., bioluminescent detection reagents), probes, amplification oligonucleotides, and the like. In some embodiments, kits include all components necessary, sufficient or useful for detecting levels of AI-2 and/or the presence of specific species of bacteria (e.g., reagents, controls, instructions, etc.). The kits described herein find use in research, therapeutic, screening, and clinical applications.

Figure 10:
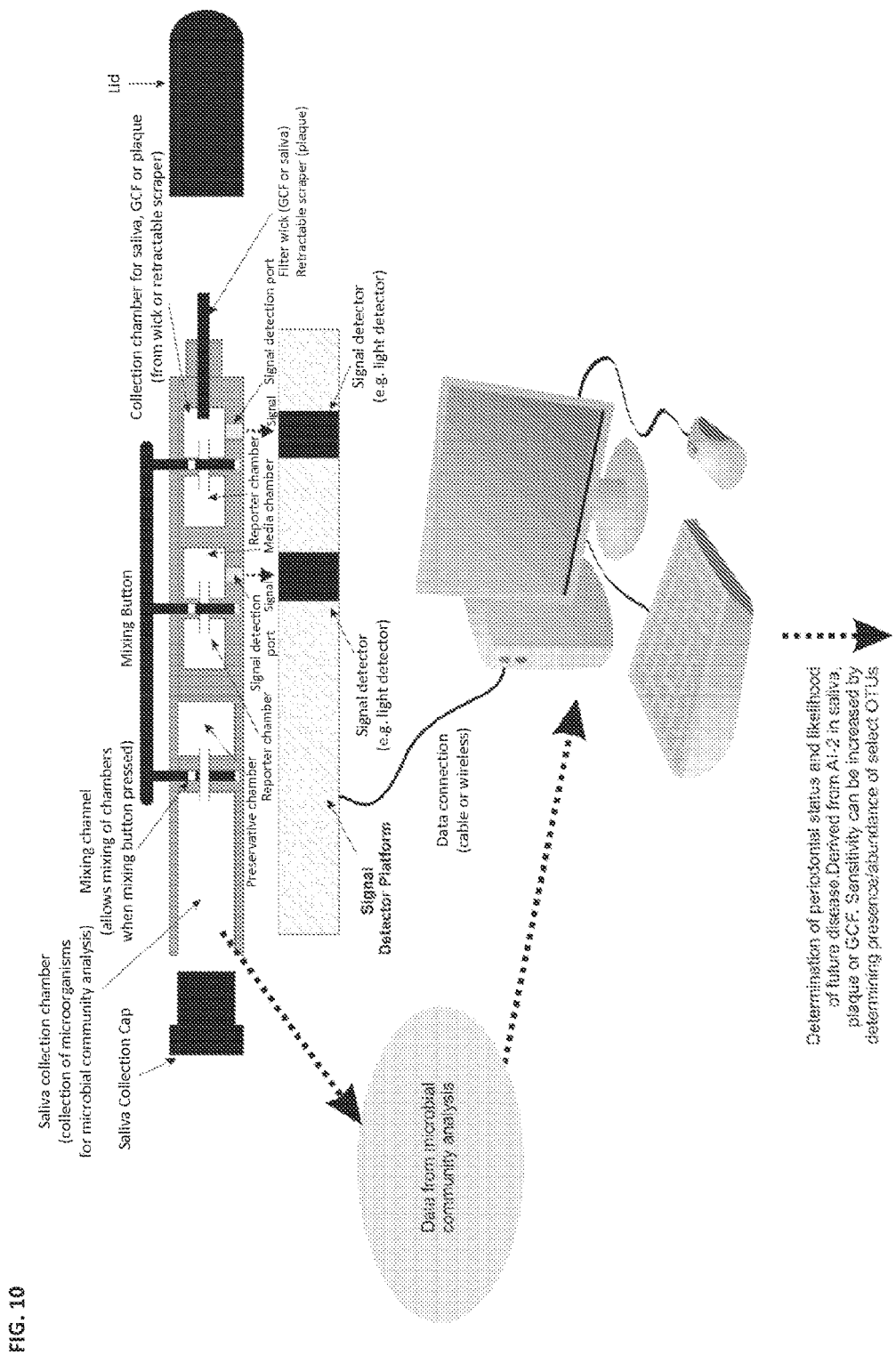
FIG. 10 shows an example of a model system for use in determining periodontal disease status of an individual.

An example of a detection system is shown in FIG. 10. In some embodiments, the system utilizes a bioluminescence assay. For example, in some embodiments, systems include a sample collection component (e.g., wick or scraper), mixing/sample preparation component, detection/signal component, and computer system (e.g., comprising a computer processor, computer memory, display screen, etc.).

EXPERIMENTAL

The following examples are provided in order to demonstrate and further illustrate certain preferred embodiments and aspects of the present invention and are not to be construed as limiting the scope thereof.

Example 1

Methods
Experimental Protocol:

A summary of the experimental protocol to obtain samples and testing procedures is as follows. To minimize degradation of AI-2, all collected samples were frozen at −80° C. prior to transport to the lab for evaluation in the *V. harveyi* AI-2 bioluminescence bioreporter detection system.

AB Media:

Autoinducer Bioassay medium (AB) was used to obtain *V. harveyi* cultures (Greenberg, E. P., J. W. Hastings, and S. Ulitzur. 1979. Induction of luciferase synthesis in Beneckeaharveyi by other marine bacteria. Arch. Microbiol. 120: 87-91). The medium consisted of 8.75 g NaCl, 8.0 g $MgSO_4*7H_2O$, 1.0 g casamino acids, adjusted to pH 7.5 with KOH in a volume of 480 mL $H_2O$ and then autoclaved. The medium was allowed to cool and sterile solutions of the following where added: 3.1 mL 1.0 M $K_2HPO_4$, 1.9 mL 1.0 M $KH_2PO_4$, 5.0 mL 0.1 M L-arginine, followed by 10 mL 50% glycerol. The final volume of the medium was 500 mL.

Detection of AI-2 Using the *V. harveyi* Bioluminescence Assay:

Using a protocol similar to the approach described by Rickard et al. (2008) Appl Microbiol. 105(6):2096-103) strains of *V. harveyi* BB 170 and *V. harveyi* BB152 were grown and prepared for AI-2 detection assays. Specifically, *V. harveyi* BB170 were grown for approximately 12 hours in AB medium at 30° C. and then diluted 1:500 in fresh AB and frozen at −80° C. in 12 ml aliquots. These frozen aliquots were used one at a time for each experiment (using a microplate) in a Victor X3 Perkin Elmer 2030 Multilabel Reader (Perkin Elmer, Waltham, Mass.). The cell-free supernatant from approximately 12 h batch culture grown *V. harveyi* BB152 (grown in AB medium) was obtained by passing the cells through a 0.22 μm filter membrane and stored at −80° C. in 200 μL aliquots.

Preparation of Control Saliva:

Saliva was collected from 5 healthy individuals. Individuals were non-smokers and had not eaten or drank (expect water) 2 hr before donating. Saliva was pooled and placed into multiple 2 mL Eppendorf microcentrifuge tubes. The saliva was centrifuge for 20 min at 13,200 rpm and subsequently filter sterilized through a 0.22 μm filter. The filter sterilized supernatant was pooled into a 15 mL falcon tube and allowed to sit overnight at room temperature in the dark before use.

Chemically Synthesized DPD Standards:

(S)-4,5-Dihydroxy-2,3-Pentanedione, Commonly Referred to as DPD, is a Chemically synthesized form of AI-2. A DPD ladder ranging from 0.1 mM-0.1 nM was used to standardize AI-2 assays. DPD was obtained from OMM Scientific (Dallas, Tex.).

Gingival Crevicular Fluid (GCF) Samples: GCF Samples.

Gingival crevicular fluid (GCF) was absorbed in Periopaper™ (Oraflow, Smithtown, N.Y.) from 12 teeth sites that were then placed separately in sterile microcentrifuge tubes and frozen at −80° C. When needed for testing, the samples were allowed to thaw at room temperature. Where-by the sample-laden Periopaper™ samples were applied to the *V. harveyi* bioluminescence AI-2 assay.

Plaque Samples:

Plaque scrapings were suspended in 100 μl of PBS (Gibco® PBS pH 7.4 1×) from 12 teeth site (same sites as the GCF) and frozen in a −80° C. freezer. Samples were allowed to thaw at room temperature. Samples were vortexed for 30 s. Samples were centrifuged for 20 min at 13,200 RPM. Cell-lacking supernatants were subsequently used as the sample for the AI-2 assay. For the AI-2 assay, each plaque sample was analyzed in triplicate.

Saliva Samples:

Unstimulated saliva was collected and subject to centrifugation at 13,200 RMP for 20 min. Cell-lacking supernatants were subsequently used as the sample for the AI-2 assay. For the AI-2 assay, each plaque sample was evaluated in two triplicate tests (two saliva samples per patient; a total of six wells).

Statistical Analysis:

Graphs, tables and statistical analysis were performed in SAS (Cary, N.C.).

Example 2

Statistical Analysis on the Relationship Between Autoinducer 2 (AI-2) and Periodontal Disease Table 1 shows summary statistics on subject characteristics.

TABLE 1

| Participant characteristics (N = 20) | |
|---|---|
| Characteristics | Number (%) |
| Age | 46 (15)[1] |
| Gender | |
| Male | 7 (35) |
| Female | 13 (65) |
| Race | |
| African American | 6 (30) |
| Asian | 2 (10) |
| Caucasian | 12 (60) |
| Disease status | |
| Healthy | 3 (15) |
| Gingivitis | 7 (35) |
| Mild | 7 (35) |
| Severe | 3 (15) |

[1]mean (SD)

AI-2 Bioluminescence

This is based upon absolute numbers after log transformation.

1. Whole Saliva (WS) Sample

FIG. 1 shows distributions of the log transformed AI-2 expression levels. Many biological response variables have log-normal distributions which do not meet the normality assumption of parametric statistical tests. This study explored the distribution of the response variable and applied the log transformation (base-10) prior to the model fitting.

Analysis of Variance (ANOVA) for Equivalence of $Log_{10}$ (AI-2) Level

| | Degree of freedom | Mean squared error | F-value | P-value |
|---|---|---|---|---|
| Disease Status | 3 | 5.841 | 17.78 | <0.0001 |
| Residuals | 116 | 0.329 | | |

The means of log of AI-2 bioluminescence from different disease status (healthy, gingivitis, mild and sever periodontal diseases) are not equal. This test treats each outcome as from an independent subject and ignores the correlation within the triplicates. Note, for each saliva sample it is actually 2×3 (6) tests.

Linear Mixed Model for $Log_{10}$(AI-2) Level (Replicate, R=6)

| Effect | Estimate (95% CI) | P-value |
|---|---|---|
| Race (vs. Caucasian) | | |
| African American | 0.55 (0.03, 1.07) | 0.06 |
| Asian | 1.20 (0.45, 1.95) | 0.007 |
| Disease Status (vs. Healthy) | | |
| Gingivitis | −0.22 (−0.97, 0.47) | 0.54 |
| Mild | −0.02 (−0.71, 0.67) | 0.95 |
| Severe | 1.27 (0.41, 2.12) | 0.01 |

A linear mixed model (LMM) can handle data where observations are not independent. In this study, the fitted LMM with random intercepts was of the form: $Y_{ij}=\beta_0+\beta_1 Race_i+\beta_2 Disease_i+b_i+e_{ij}$, where $Y_{ij}$ refers to the outcome AI-2 for subject i at $j^{th}$ replicated assay, $Disease_i$ represents the 4-level disease status for subject i, $Race_i$ is a subject-specific variable, $b_i$ is the random intercept for subject i, and is the independently distributed residual error for subject i at $j^{th}$ replicated assay. A compound symmetry covariance structure among residual errors within subject was used. This model choice was determined by the Akaike information criterion (AIC). Effects associated with 1 unit increase in the log of AI-2 bioluminescence were estimated.

An increase for Asian in AI-2 level was identified (P=0.007). There was a significant relationship between severe periodontal disease (compared to healthy) and AI-2 level (P=0.01).

2. Gingival Crevicular Fluid (GCF) Sample

Figure 2:
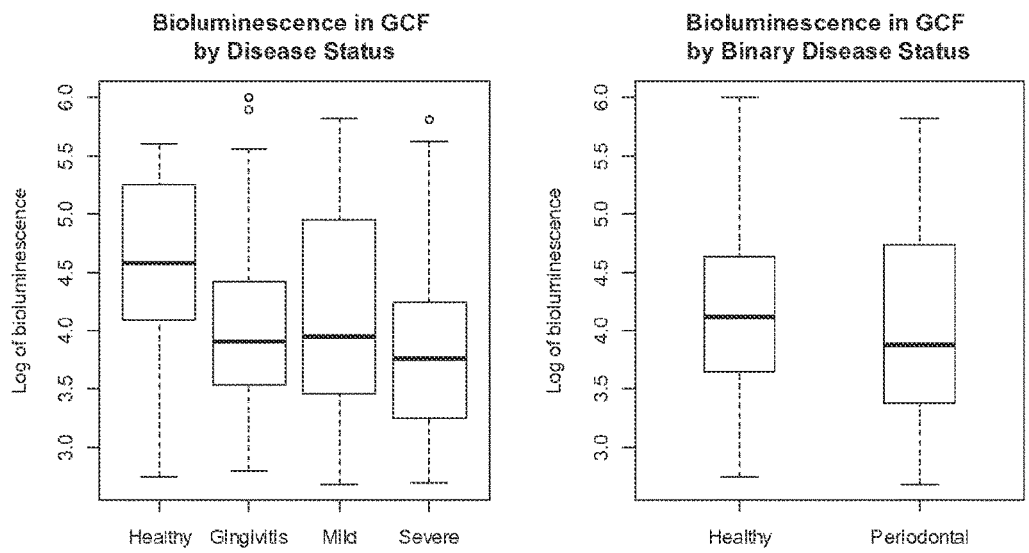
FIG. 2 shows AI-2 expression in gingival crevicular fluid (GCF) by disease status and binary disease status.

FIG. 2 shows a plot of bioluminescence in GCF by disease status and binary disease status.

(2) ANOVA

|  | Degree of freedom | Mean squared error | F-value | P-value |
| --- | --- | --- | --- | --- |
| Disease Status | 3 | 4.214 | 7.17 | 0.0001 |
| Residuals | 236 | 0.587 | | |

The means of log of AI-2 bioluminescence from different disease status (healthy, gingivitis, mild and sever periodontal diseases) are not equal, when treating each outcome as from an independent subject and ignoring the correlation of teeth within the same subject.

(3) Mixed Model

| Effect Disease Status (vs. Healthy) | Estimate (95% CI) | P-value |
| --- | --- | --- |
| Gingivitis | −0.60 (−1.27, 0.08) | 0.10 |
| Mild | −0.43 (−1.10, 0.24) | 0.23 |
| Severe | −0.77 (−1.56, 0.03) | 0.08 |

Method: the fitted LMM with random intercepts had the same form:

$Y_{ij}=\beta_0+\beta_1 Race_i+\beta_2 Disease_i+b_i+e_{ij}$, where $Y_{ij}$ refers to the outcome AI-2 for subject i at $j^{th}$ tooth, $Race_i$ and $Disease_i$ are subject-specific variables, $b_i$ is the random intercept for subject i, and $e_{ij}$ is the independently distributed residual error for subject i at $j^{th}$ tooth. Again, this model choice was determined by the AIC.

There was no difference among disease status in the expression level of AI-2 after justifying the correlation of measurements taken from different teeth within the same subject. This might be due to biological or technique driven effects.

Figure 3:
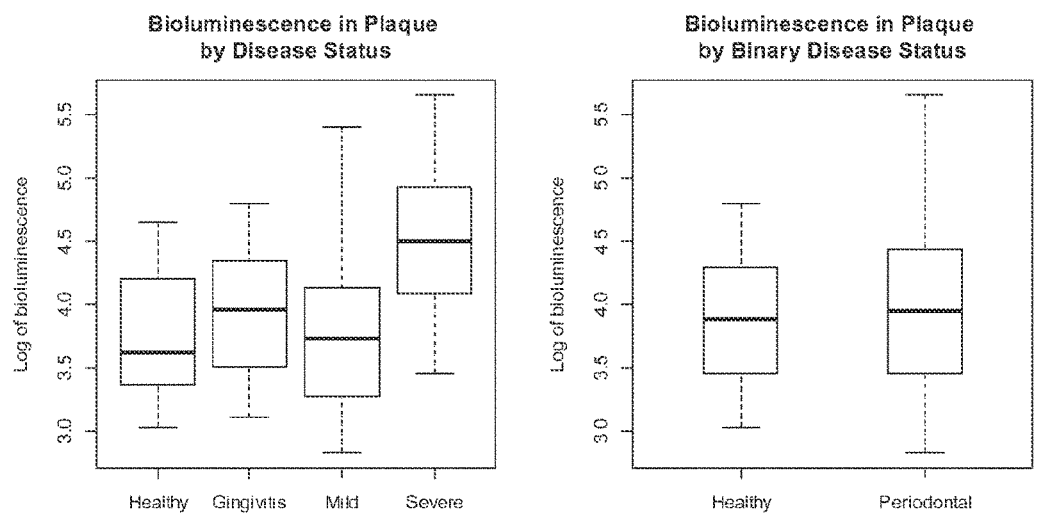
FIG. 3 shows AI-2 expression in plaque by disease status and binary disease status.

FIG. 3 shows bioluminescence in plaque samples.

(2) ANOVA

|  | Degree of freedom | Mean squared error | F-value | P-value |
| --- | --- | --- | --- | --- |
| Disease Status | 3 | 13.773 | 49.4 | <0.0001 |
| Residuals | 716 | 0.279 | | |

The means of log of AI-2 bioluminescence from different disease status (healthy, gingivitis, mild and sever periodontal diseases) are not equal, when treating each outcome as from an independent subject and ignoring the correlation of teeth and replicates within the same subject.

(3) Mixed Model

| Effect Disease Status (vs. Healthy) | Estimate (95% CI) | P-value |
| --- | --- | --- |
| Gingivitis | 0.16 (−0.27, 0.58) | 0.48 |
| Mild | −0.01 (−0.44, 0.41) | 0.95 |
| Severe | 0.68 (0.17, 1.18) | 0.02 |

Method: here, the fitted LMM has nested random effects and was of the form:

$Y_{ijk}=\beta_0+\beta_1 Race_i+\beta_2 Disease_i+b_i+e_{ijk}$, where $Y_{ijk}$ refers to the outcome AI-2 for the $j^{th}$ tooth of subject i at $k^{th}$ repeated assay, $Race_i$ and $Disease_i$ are subject-specific variables, $b_i$ is the random intercept for subject i, $b_{ij}$ is the random intercept for the $j^{th}$ tooth of subject i, and $e_{ijk}$ is the independently distributed residual error for the $j^{th}$ tooth of subject i at $k^{th}$ replication. Again, this model choice was determined by the AIC.

There was a significant relationship between severe periodontal disease (compared to healthy) and AI-2 level (P=0.02).

AI-2 Relative Bioluminescence

"Relative bioluminescence" refers to a different approach to examine the data. Specifically, the amount of bioluminescence is divided by the control for each plate/run. This has advantages and disadvantages over the previous approach—for example the detector strains and AI-2 controls were discovered to change their sensitivity over time. However, this is a more often used approach, but there is no precedent for this type of long term study.

Figure 4:
FIG. 4 shows log fold induction of AI-2 expression in whole saliva by disease status and binary disease status.

FIG. 4 shows log fold induction in whole saliva (WS).

(2). ANOVA for Equivalence of $Log_{10}(AI-2)$ Relative Bioluminescence

|  | Degree of freedom | Mean squared error | F-value | P-value |
| --- | --- | --- | --- | --- |
| Disease Status | 3 | 0.608 | 1.54 | 0.21 |
| Residuals | 116 | 0.394 | | |

There is no significant difference among disease status (healthy, gingivitis, mild and sever periodontal diseases) with regard to the mean of log of relative bioluminescence.

Figure 5:
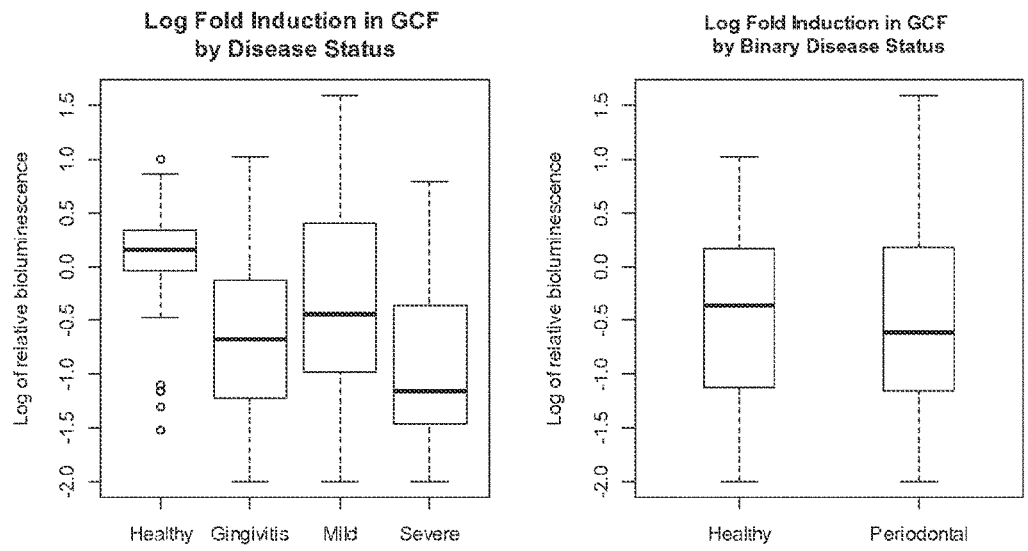
FIG. 5 shows log fold induction of AI-2 expression in GCF by disease status and binary disease status.

FIG. 5 shows log fold induction in gingival crevicular fluid (GCF) sample.

(2) ANOVA

|  | Degree of freedom | Mean squared error | F-value | P-value |
| --- | --- | --- | --- | --- |
| Disease Status | 3 | 7.315 | 12.56 | <0.0001 |
| Residuals | 236 | 0.582 | | |

The means of log of AI-2 relative bioluminescence from different disease status (healthy, gingivitis, mild and sever periodontal diseases) are not equal.

(3) Mixed Model

| Effect Disease Status (vs. Healthy) | Estimate (95% CI) | P-value |
| --- | --- | --- |
| Gingivitis | −0.69 (−1.35, −0.03) | 0.06 |
| Mild | −0.35 (−1.01, 0.31) | 0.31 |
| Severe | −0.97 (−1.76, −0.19) | 0.03 |

There was a significant relationship between severe periodontal disease (compared to healthy) and AI-2 level (P=0.03). Additionally, a mild effect of having gingivitis was found for the log of fold induction in GCF sample (P=0.06).

Figure 6:
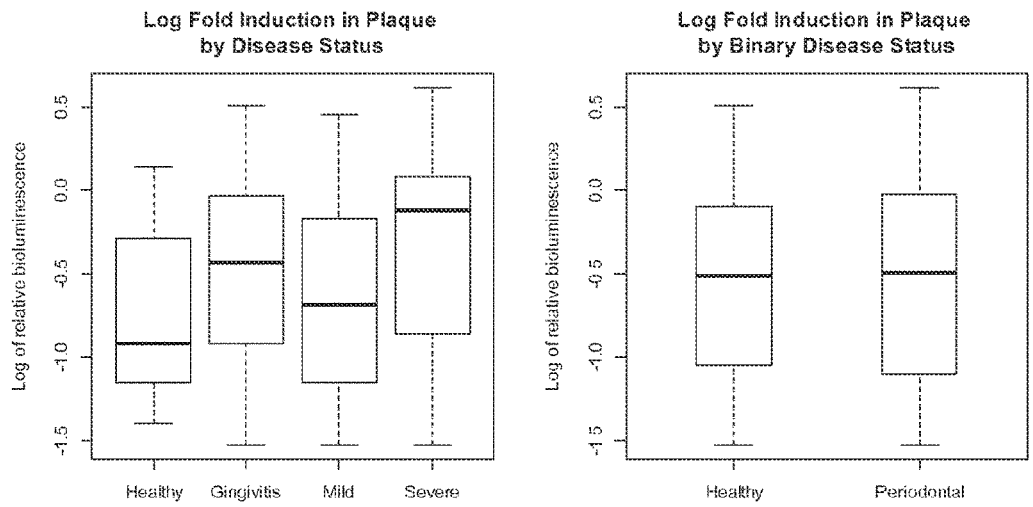
FIG. 6 shows log fold induction of AI-2 expression in plaque by disease status and binary disease status.

FIG. 6 shows log fold induction in plaque.

(2) ANOVA

|  | Degree of freedom | Mean squared error | F-value | P-value |
|---|---|---|---|---|
| Disease Status | 3 | 3.972 | 13.63 | <0.0001 |
| Residuals | 716 | 0.291 | | |

The means of log of AI-2 relative bioluminescence from different disease status (healthy, gingivitis, mild and sever periodontal diseases) are not equal.

(3) Mixed Model

| Effect Disease Status (vs. Healthy) | Estimate (95% CI) | P-value |
|---|---|---|
| Gingivitis | 0.28 (−0.18, 0.73) | 0.25 |
| Mild | 0.09 (−0.36, 0.55) | 0.69 |
| Severe | 0.38 (−0.16, 0.92) | 0.19 |

The mixed model indicated there was no difference among disease status in the relative bioluminescence of AI-2 after justifying the multilevel correlation where teeth are nested within subjects, and each tooth has multiple measurements.

Example 3

Figure 7:
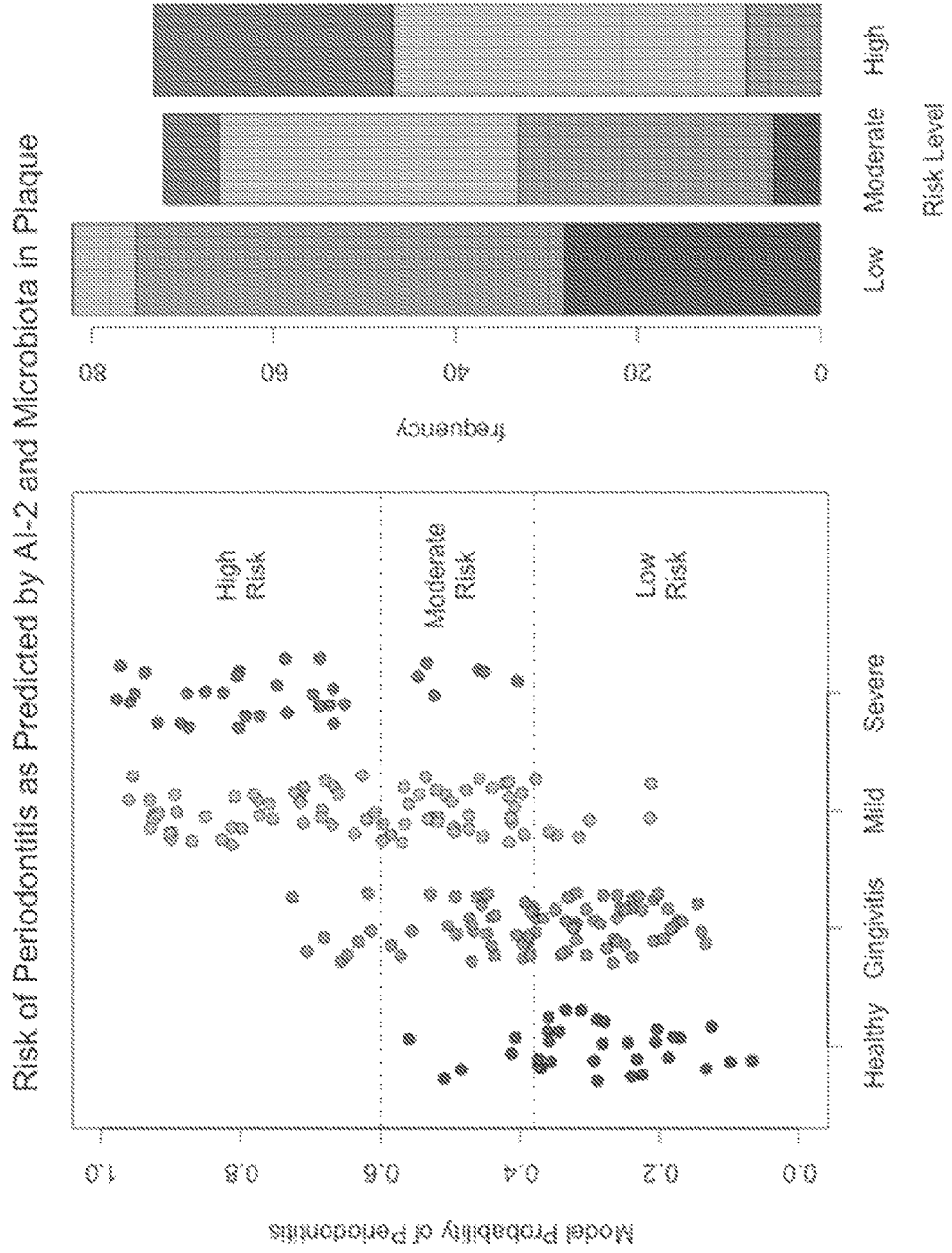
FIG. 7 shows disease state predicted by AI-2 and microbiota in plaque. Microbiota are used as complementary reference/guide sequences (referred to as operational taxonomic units, OTUs) to strengthen sensitivity.
Figure 8:
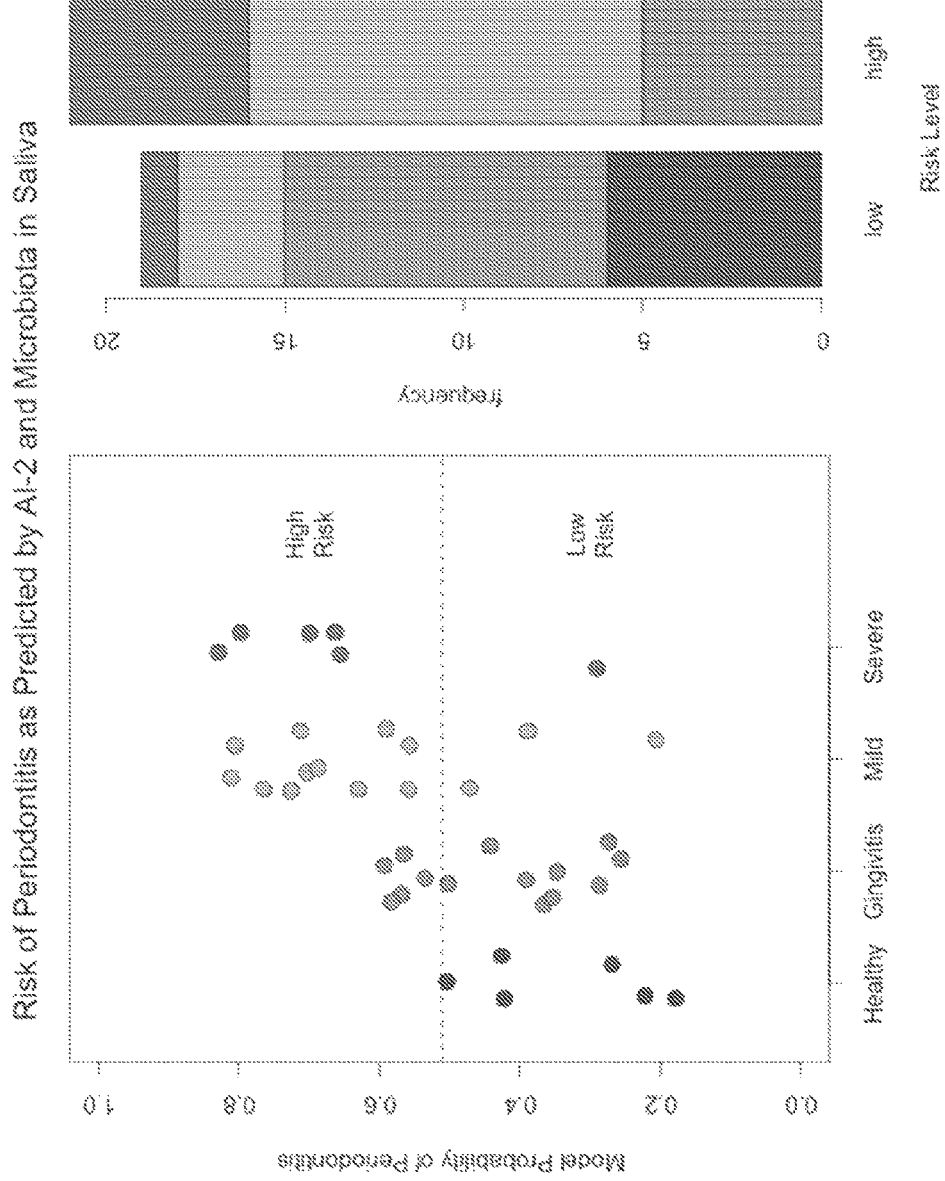
FIG. 8 shows disease state predicted by AI-2 and microbiota in saliva. Microbiota are used as complementary reference/guide sequences (referred to as operational taxonomic units, OTUs) to strengthen sensitivity.
Figure 9:
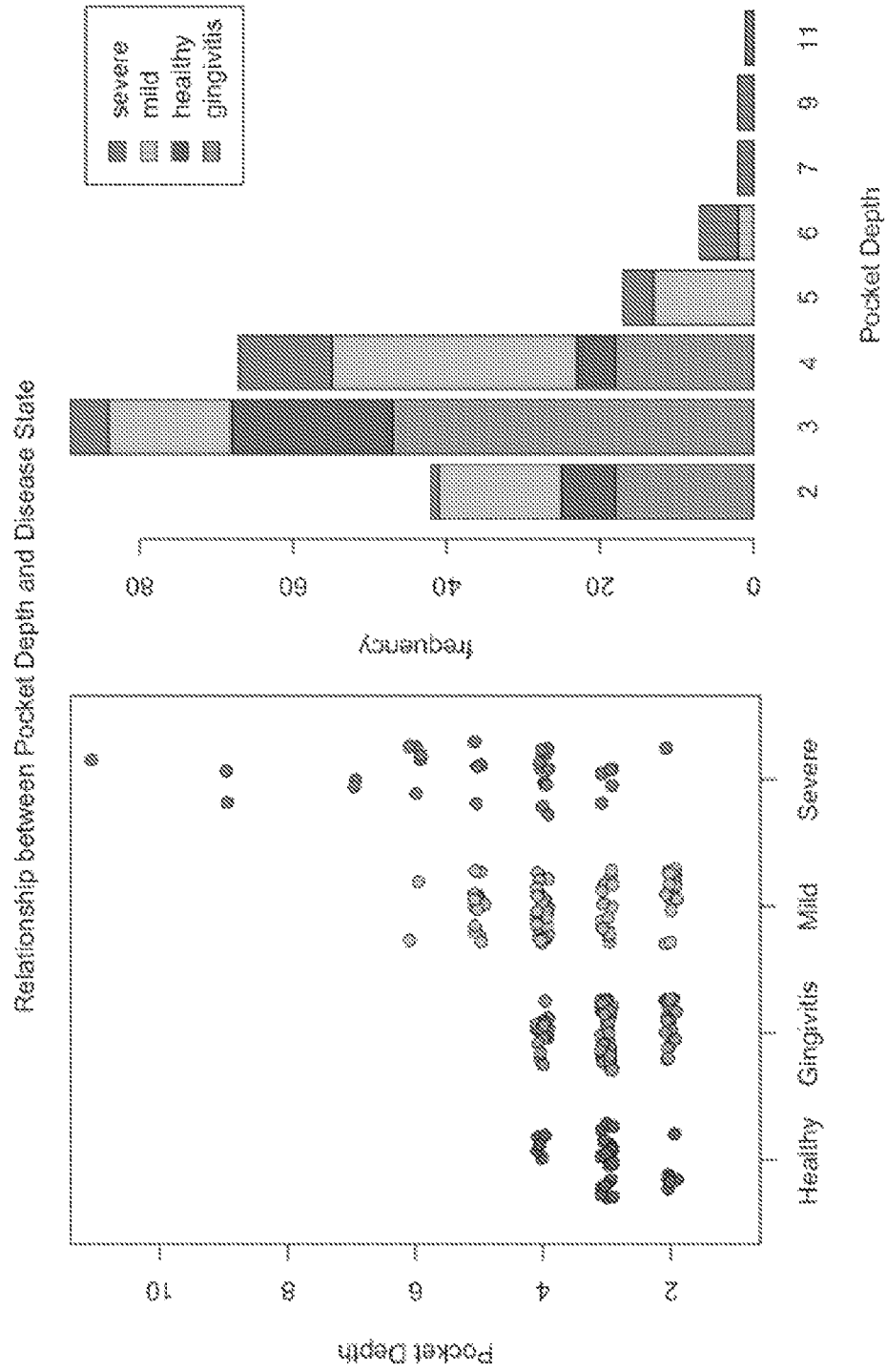
FIG. 9 shows an example of correlation of actual pocket depth against predicted pocket depth derived from AI-2 data and microbial community data.

This example describes the use of AI-2 levels in combination with microbial community analysis to increase sensitivity of approach to determine periodontal disease status Using Random Forest, a machine learning algorithm (decision tree software), AI-2 levels (as determined by bioluminescence or other approaches) were analyzed in conjunction with the microbial community (See Tables of species below) to enable an even more sensitive approach to determining periodontal disease and to establish risk of an individual/patient transitioning from a healthy to periodontal disease state. Increased risk highlights the need for treatment. Examples of threshold states are shown in FIGS. 7 and 8. Predictions were checked against actual clinical markers, such as pocket depth, as shown in FIG. 9.

AI-2 levels in plaque, GCF, and/or saliva can be determined by a device such as the device (FIG. 10) that can also collect saliva or other oral material for microbiological analysis (to determine the microbial community composition).

Most Predictive OTUs in Combination with AI-2 Levels in Plaque

| OTU | Classification |
|---|---|
| Otu00041 | *Akkermansia muciniphila* |
| Otu00015 | *Bacteroides ovatus* |
| Otu00002 | *Veillonella dispar* |
| Otu00042 | *Coprobacter fastidiosus* |
| Otu00040 | *Ruminococcus gnavus* |
| Otu00070 | *Blautia schinkii* |
| Otu00003 | *Streptococcus oralis* |
| Otu00017 | *Bacteroides vulgatus* |
| Otu00023 | *Rothia dentocariosa* |
| Otu00031 | *Leptotrichia wadei* |
| Otu00012 | *Bacteroides uniformis* |
| Otu00009 | *Neisseria subflava* |
| Otu00016 | *Actinomyces oris* |
| Otu00056 | *Bacteroides stercoris* |
| Otu00011 | *Haemophilus parainfluenzae* |
| Otu00063 | *Selenomonas flueggei/noxia* |
| Otu00208 | *Abiotrophia defectiva* |
| Otu00010 | *Corynebacterium matruchotii* |
| Otu00068 | Unclassified Flavobacteriaceae |

Most Predictive OTUs in Combination with AI-2 Levels in Saliva

| OTU | Classification |
|---|---|
| Otu00009 | *Neisseria cinerea* |
| Otu00063 | *Selenomonas* sp. |
| Otu00002 | *Veillonella dispar* |
| Otu00156 | *Oribacterium sinus* |
| Otu00022 | *Leptotrichia buccalis* |
| Otu00015 | *Bacteroides ovatus* |
| Otu00037 | *Porphyromonas catoniae* |
| Otu00078 | *Streptococcus salivarius* |
| Otu00017 | *Bacteroides vulgatus* |
| Otu00179 | *Akkermansia muciniphila* |
| Otu00020 | *Kingella denitrificans* |
| Otu00068 | *Bergeyella* sp. AF14 |
| Otu00011 | *Haemophilus parainfluenzae* |
| Otu00001 | *Fusobacterium nucleatum* |
| Otu00021 | Unclassified Porphyromonadaceae |
| Otu00040 | *Ruminococcus gnavus* |
| Otu00013 | *Prevotella melaninogenica* |
| Otu00116 | Unclassified Bacteroidetes |
| Otu00023 | *Rothia dentocariosa* |

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

The invention claimed is:

1. A method of diagnosing periodontal disease, comprising;
   a) detecting: a1) an altered level of Autoinducer-2 (AI-2) in an oral sample; and a2) the presence of one or more bacteria in said oral sample, wherein said bacteria are one or more species selected from the group consisting of *Akkermansia muciniphila, Coprobacter fastidiosus, Blautia schinkii, Bergeyella* sp. AF14, and *Ruminococcus gnavus*, and
   b) diagnosing the presence of periodontal disease when said level of AI-2, and said bacteria are altered relative to the level in subjects not diagnosed with periodontal disease.

2. The method of claim 1, wherein said oral sample is an oral fluid or a plaque sample.

3. The method of claim 2, wherein said oral fluid is saliva or gingival crevicular fluid (GCF).

4. The method of claim 1, wherein said oral sample is plaque and said bacteria are one or more species selected from the group consisting of *Akkermansia muciniphila, Coprobacter fastidiosus, Blautia schinkii* and *Ruminococcus gnavus*.

5. The method of claim 1, wherein said oral sample is saliva and said bacteria are one or more species selected from the group consisting of *Akkermansia muciniphila, Bergeyella* sp. AF14, and *Ruminococcus gnavus*.

6. The method of claim 1, wherein said one or more species are 5 or more species.

7. The method of claim 1, wherein said one or more species are all of said species.

8. The method of claim 1, further comprising the step of administering a treatment for periodontal disease when said altered level of AI-2 are detected.

9. The method of claim 8, wherein said treatment is selected from an antibiotic, a dental cleaning, and a laser treatment.

10. The method of claim 8, wherein said treatment is in a mouthwash or toothpaste.

11. The method of claim 1, wherein said levels of AI-2 are increased or decreased relative to the level in subjects not diagnosed with periodontal disease.

12. The method of claim 1, wherein compounds that alter the levels of AI-2 or the presence of said bacteria in said sample relative to the levels in the absence of the compounds are identified as therapeutic agents.

13. The method of claim 1, wherein said oral sample is saliva or and said bacteria are *Akkermansia muciniphila, Ruminococcus gnavus* or a combination thereof.

* * * * *